(12) United States Patent  (10) Patent No.: US 9,046,548 B2
Beyeler et al.  (45) Date of Patent: Jun. 2, 2015

(54) SYSTEM FOR MECHANICAL CHARACTERIZATION OF MATERIALS AND BIOLOGICAL SAMPLES IN THE SUB-MILLINEWTON FORCE RANGE

(75) Inventors: Felix Beyeler, Regensdorf (CH); Simon Muntwyler, Zurich (CH)

(73) Assignee: Femtotools AG, Buchs Zh (CH)

( * ) Notice: Subject to any disclaimer, the term of this patent is extended or adjusted under 35 U.S.C. 154(b) by 537 days.

(21) Appl. No.: 13/497,322

(22) PCT Filed: Aug. 30, 2010

(86) PCT No.: PCT/EP2010/062606
§ 371 (c)(1),
(2), (4) Date: Apr. 13, 2012

(87) PCT Pub. No.: WO2011/032819
PCT Pub. Date: Mar. 24, 2011

(65) Prior Publication Data
US 2012/0186365 A1  Jul. 26, 2012

(30) Foreign Application Priority Data

Sep. 21, 2009 (EP) ..................................... 09170860

(51) Int. Cl.
*G01L 1/00* (2006.01)
*G01L 1/10* (2006.01)
*G01Q 30/02* (2010.01)
*B81C 99/00* (2010.01)
*B82Y 35/00* (2011.01)
*G01B 9/04* (2006.01)
*G02B 21/32* (2006.01)

(52) U.S. Cl.
CPC ............ *G01Q 30/025* (2013.01); *B81C 99/003* (2013.01); *B82Y 35/00* (2013.01); *G01B 9/04* (2013.01); *G01N 2203/0089* (2013.01); *G01N 2203/0286* (2013.01); *G02B 21/32* (2013.01)

(58) Field of Classification Search
USPC ....................................... 73/862.541, 862.625
See application file for complete search history.

(56) References Cited

U.S. PATENT DOCUMENTS

| 2005/0034543 A1* | 2/2005 | Xi et al. ................... 73/862.634 |
| 2006/0196280 A1* | 9/2006 | Xi et al. ................... 73/862.625 |
| 2012/0186365 A1* | 7/2012 | Beyeler et al. ........... 73/862.541 |
| 2013/0247682 A1* | 9/2013 | Oh et al. ......................... 73/826 |
| 2014/0004345 A1* | 1/2014 | Chasiotis et al. ............. 428/399 |

FOREIGN PATENT DOCUMENTS

| JP | 11347971 A | * 12/1999 | ................ B25J 7/00 |
| JP | 2008284686 A | * 11/2008 | |
| WO | WO 2010112242 A1 | * 10/2010 | ................ G01L 1/14 |

* cited by examiner

*Primary Examiner* — Lisa Caputo
*Assistant Examiner* — Jamel Williams
(74) *Attorney, Agent, or Firm* — Laurence A. Greenberg; Werner H. Stemer; Ralph E. Locher

(57) ABSTRACT

The mechanical characterization system includes three main parts: A sub-millinewton resolution capacitive force sensor, at least one micromanipulator with position measurement capabilities, and a microscope. The sensitive axis of the force sensor is adjustably connected via adaptor pieces to the micromanipulator at any angular orientation relative to the sample holder.

14 Claims, 2 Drawing Sheets

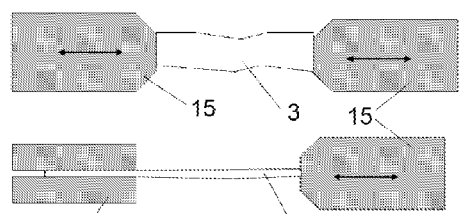
FIG. 3A
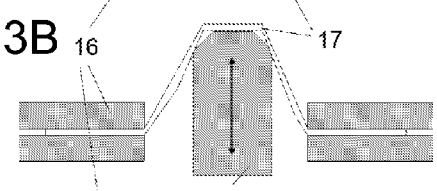
FIG. 3B
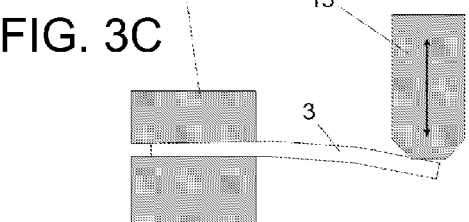
FIG. 3C
FIG. 3D
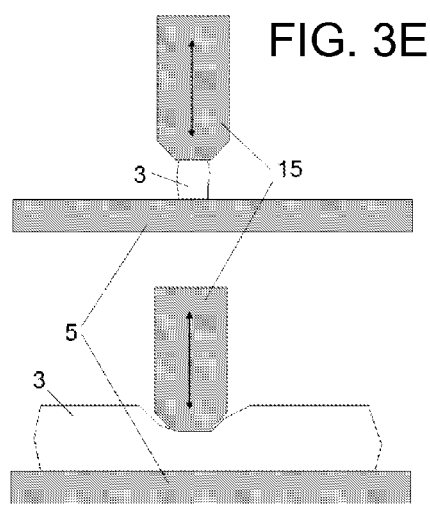
FIG. 3E
FIG. 3F

SYSTEM FOR MECHANICAL CHARACTERIZATION OF MATERIALS AND BIOLOGICAL SAMPLES IN THE SUB-MILLINEWTON FORCE RANGE

BACKGROUND OF THE INVENTION

Field of the Invention

The present invention relates to a system for mechanical characterization of materials and biological samples in the sub-millinewton force range, and to the mechanical characterization of sub-millimeter sized sample areas on a sample holder.

Biological systems such as tissue, cells or protein fibers are highly deformable materials with mechanical properties which are normally not well known. The size of most individual animal or human cells are in the range of 1 µm to 100 µm. Quantitative measurements of the forces in these miniature systems are the base for the emerging new field of mechanobiology. Mechanobiology studies the interaction between mechanical load and biological processes on the level of organisms, tissues, cells or cell sub-systems. It is relevant in many areas of physiology, medicine, and biomedical device design. Other fields in research and industry depend on the accurate measurement of sub-millinewton forces. In microsystems development and characterization, force sensing is an important objective. Friction and micro-indentation measurements are performed in material science. Also, the forces dominating micro-robotic and nano-robotic tasks such as pick-and-place operations and assembly tasks are in the range of micronewtons. The interdisciplinary research fields listed above benefit from the development of reliable, highly accurate micro force sensing tools. Micro-electromechanical systems (MEMS) technology enables the fabrication of miniaturized force sensing devices.

The state of the art can be summarized as follows:

The Paper In situ mechanical characterization of mouse oocytes using a cell holding device [1] discloses: Polymer posts are used for force sensing rather than a capacitive force sensor. The system does not allow the direct measurement of position and force. Microscope images have to be processed to obtain position information. The force sensor cannot be oriented horizontally or at an angle.

The system according to <<Mechanical Analysis of Chorion Softening in Prehatching Stages of Zebrafish Embryos>> [2] reveals no micromanipulators with positing measurement capabilities (encoders). The system does even not allow the direct measurement of position and force. Microscope images have to be processed to obtain position information.

The system according to <<A newly designed tensile tester for cells and its application to fibrobroblasts>> [3] reveals no micromanipulators with positing measurement capabilities (encoders). The system does not allow the direct measurement of position and force. Microscope images have to be processed to obtain position information. Strain gauges are used for force sensing rather than a capacitive force sensor.

The mechanical characterization of microscopic objects is a big challenge due to the small forces and the small deformations that have to be measured. The mechanical characterization may include the measurement of the Youngs-modulus, elastic and plastic deformation, hysteresis, breaking strength, adhesion properties as well as the topography of the sample. Typically, the forces are in the sub-milli-Newton range and the deformations are in the nano-meter to millimeter range.

BRIEF SUMMARY OF THE INVENTION

The goal of the present invention is therefore to provide a system for mechanical characterization of Materials and Biological Samples in the sub-Millinewton Force Range according to the below mentioned requirements.

This goal is reached by a system specified with the features as claimed.

Conventional systems can normally only be used for one specific type of sample. Forces and deformations can only be applied in one specific direction, which requires extensive sample preparation. Also, conventional systems often times cannot directly measure both the force applied to the sample and the deformation. Position information is then measured by a vision system (being part of a mechanical characterization system) which requires a post-processing of the images. The mechanical characterization system can be applied for a large variety of samples in the sub-mm range. This is achieved by a design which enables the adjustment of the sensing direction of the force sensor. Rotating the sample is not required. Integrated encoders in the manipulators simultaneously measure the position and deformation of the sample without the need of processing images acquired by a vision system. Capacitive force sensors are used as force transducers, featuring a high resolution while having a compact size which is important due to the limited space between the sample and the microscope lens.

Embodiments of the invention are now described in further details with reference to the accompanying drawings in which are depicted:

BRIEF DESCRIPTION OF THE SEVERAL VIEWS OF THE DRAWING

FIG. 3a) to FIG. 3f)
Different sensing configurations for the measurement of mechanical properties using the mechanical characterization system.

DESCRIPTION OF THE INVENTION

Figure 1:
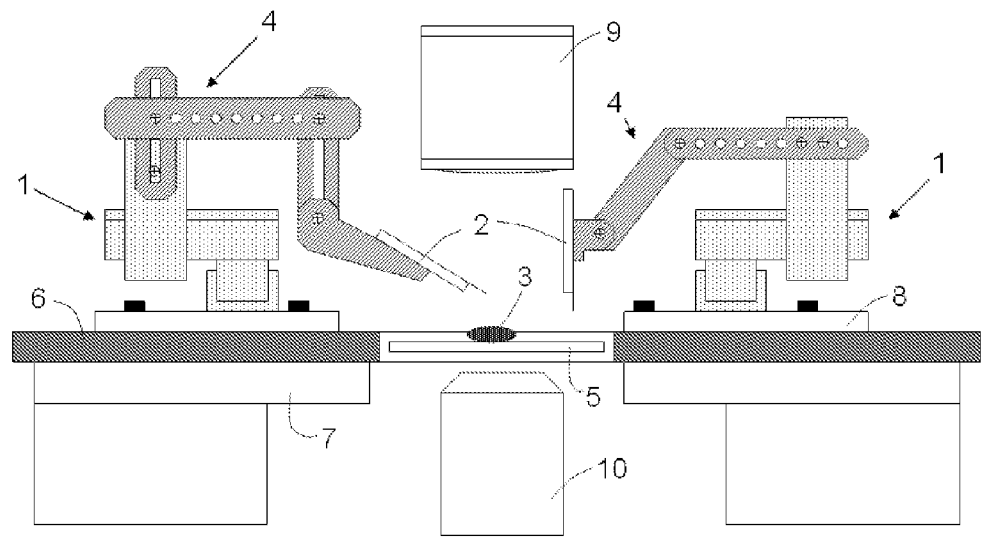
FIG. 1
First embodiment of a mechanical characterization system.

A first embodiment of the mechanical characterization system according to FIG. 1 consists of three main parts: First is a sub-mN resolution capacitive force sensor 2. Second is at least one micromanipulator 1 and third is a microscope 10. The sample 3 to be tested can be organic or non-organic. In biological research, the sample can be a tissue, a fiber, a cell or cell components. In material science, MEMS development, or nano-science the sample can be a microfabricated structure, a wafer, a material sample with a defined geometry, a particle or an object of any other shape.

Force sensors fabricated by MEMS technology allow the measurement of sub-millinewton forces by capacitive force sensing or by piezoresistive force sensing. Also, non-MEMS sensors may be used featuring small force sensing capabilities. The drawback of these sensors is their fragility. However, by combing these sensors with micromanipulators 1 and a microscope having a microscope condenser 9 and a enables the characterization of small sized samples and perform tensile tests. The force sensor can be a capacitive force sensing MEMS probe, a capacitive cantilever-type force sensor, a force sensing microgripper or a multi-axis capacitive force sensor.

One or multiple micromanipulators 1 are mounted on a microscope. These micromanipulators 1 can be single-axis or multi-axis. The may also feature a combination of linear and rotational motion. The micromanipulators 1 can be motorized, e.g. stepper, DC motor, piezo or manual. The micromanipulators 1 include a position encoder for the measurement of the travel distance.

The connection to the microscope may be done by a mounting plate 6 or a breadboard or the micromanipulators 1 are attached to the microscope directly. The microscope may be a regular top microscope, a stereo-microscope, an inverted (biological) microscope or a digital microscope camera, a phase-contrast microscope, a confocal microscope, a fluorescence microscope, a scanning electron microscope or a tunneling microscope. In case of inverted microscopes a hole is located in the mounting plate such that the sample can be seen from below. When using a breadboard, the manipulator(s) can be placed at different locations relative to the microscope. Slides 8 may also be used to position the micromanipulators 1 relative to the microscope. Another option would be to use magnetic forces or vacuum to hold the micromanipulators 1 in place. A microscope positioning table 7 may also be used to position the micromanipulators 1 or as a substitute for the micromanipulators 1.

The capacitive force sensors 2 are mounted on the micromanipulators (or the microscope table). Adaptor pieces 4 may be used for that. These sensor adaptor pieces 4 may be a single piece or consist of multiple pieces to adjust the location of the sensor. Plates with holes or slits may be used for the easy positing of the sensors. The adaptor pieces 4 are shaped such that the sensor can be accurately moved without touching the microscope lens 10 or the microscope condenser 9 The sensor adaptor pieces 4 may be dove-tail slides. The shape of the adaptor pieces 4 is such that the sensor 2 can be positioned without touching the microscope lens or the condenser of the microscope. The adaptor pieces 4 may also include electrical connections to the force sensor 2. Alternatively, the force sensors 2 are interfaced by cables. The force sensor 2 is connected with the micromanipulator 1 at any angle of the sensitive axis of the force sensor 2 relative to the sample holder 5. The sample holder (5) and especially the probe 3 are inside the field of view of the microscope 10. The adaptor pieces 4 are designed such that the force sensors 2 can be oriented horizontally, vertically or at any other angle. This connection is preferably done with at least one sensor adaptor piece 4. The attachment of the force sensor 2 to the sensor adaptor piece 4 may be done by screws, the insertion into the electrical connector, glue or by mechanical clamping.

The sample 3 to be tested is placed on the sample holder 5, such that it can be observed by the microscope. Depending on the type of the sample different kind of sample holders 5 are used. The sample holder 5 may be attached to a rail 14, a microscope table 7, a rotational actuator or another positioning device such that the sample 3 can be moved or replaced. This positioning device also enables the change of the sample 3 without risking damaging the fragile sensors 2. For measurements in liquid, a dish type sample holder 3 or fluid channels may be used. The sample may be transported in the channels by a liquid flow.

Figure 2:
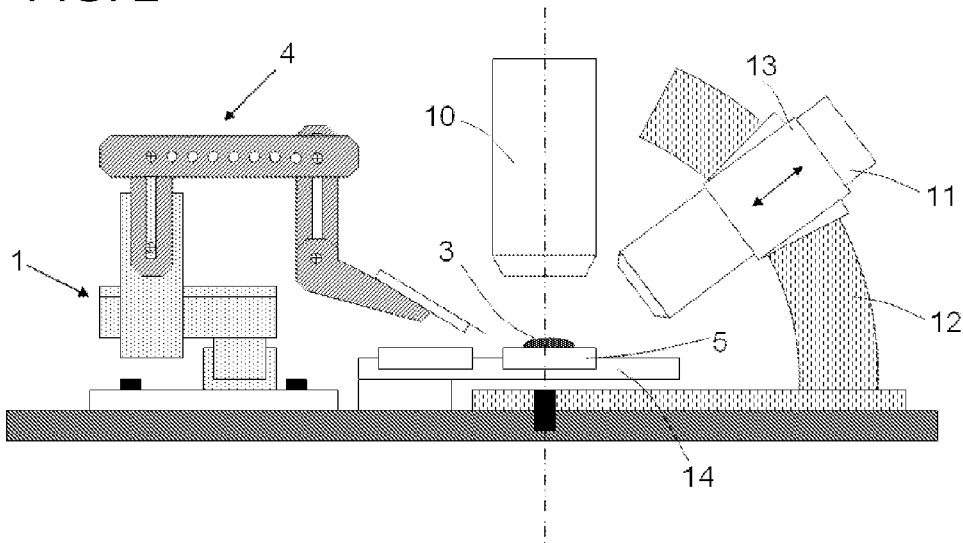
FIG. 2
Second embodiment of a mechanical characterization system.

The description refers now to FIG. 2 depicting a second embodiment of a mechanical characterization system which can be denoted also as a vision system: Optionally one or multiple microscope cameras 11 may be used to observe the sample 3 from additional viewpoints. This microscope camera 11 may be mounted in a fixed position or on a movable camera holder 12. The camera holder 12 allows a rotation around one or multiple axes such that the sample 3 always stays inside the field of view of the camera respectively of the microscope. Screws are used to fix the position of the camera holder 12. The positioning device may be attached onto the mounting plate 6 (breadboard) or the microscope directly. Slides may be used to adjust the position of the camera holder 12 relative to the sample 3. A manual or motorized stage 13 may be used to adjust the focus of the microscope camera 11. Alternatively, a microscope camera 11 with focusing capabilities can be used. A side view camera simplifies the application of the force during the measurement and allows the observation of the deformation. A microscope camera 11 with a built-in lighting system may be used.

One or multiple light sources for adjusting the lighting of the sample 3 may be used. These light sources may be light emitting diodes (LEDs), halogen lamps or fibers. Similar to the camera holder, a light holder may be used which allows the positing of the light relative to the sample. The light holder allows a rotation around one or multiple axes such that the sample always stays inside the light.

Other sensors which measure temperature and humidity may be added to the system to monitor environmental conditions. To obtain repeatable results the system may be placed inside a climate chamber or an incubator where temperature and humidity is controlled. The chamber also counteracts contamination and mechanical damage of the sample and force sensors.

The system is preferably controlled by a computer. For the connection, a USB, Firewire or Serial interface may be used. The capacitive force sensor 2 may be used to detect contact with the sample 3 or an obstacle, to avoid damages to the fragile sensor 2 and the sensitive sample 3. The force reading may also be used for force-feedback control of the manipulator input device (Joysticks). Interfacing the system with a PC may be used to make automated measurements or to scan over a certain area and measure mechanical properties of the sample and on the same time its geometry. The manipulators are automatically stopped when the force reading exceeds a critical value.

Fluorescence microscopes may be used to measure optical properties of the sample while performing the force measurement. The optical microscope may also be replaced by a scanning electron microscope. In that case the manipulators with the sensor(s) would be placed inside the vacuum chamber.

The material samples and structures which are characterized using sub-mN force sensing systems are usually very small or the area of interest on the sample is very small (size scale below 1 mm). A microgripper mounted on one of the micromanipulators may be used to do handle the objects and blades may be placed on them for slicing the sample.

One method is to apply a compression force to the sample, see FIG. 3e), FIG. 3f) or to stretch the sample while measuring both force and position of the sensor see FIG. 3a), FIG. 3b), FIG. 3c). Encoders in the manipulators may be used to measure the position. MEMS capacitive force sensors 2 feature end-effectors small enough for this task. Also, force sensing MEMS grippers may be used to apply a load to the sample. This kind of compression and tensile tests can be used to obtain stress-strain information and find mechanical properties like stiffness (Youngs modulus), linearity, yield stress and hysteresis. By simultaneously recording the time during the experiment, time dependent properties can be measured also such as visco-elasticity and ageing of the material. By pushing onto structures like membranes, cantilevers or fibers, see FIG. 3d), their mechanical properties can be derived if the geometry of the sample is known (bending tests). All tests can be performed vertically and horizontally.

In the microscale, the fixing of the sample is an issue, especially when working with fibers 17 such as muscle fibers or protein fibers. One manipulator may be used to hold the sample in place by clamps 16 or vacuum capillaries. The other manipulator has a sensor mounted on it. When doing a tensile test the sample has to be attached to the sensor also. This can be done with biocompatible glue or with chemically bond the sample to the sensor by first functionalizing the sensor. The sensor may also feature a hook-shape probe for holding and stretching the sample.

For probing very small areas or for making indentation experiments, a sharp probe 15 may be attached to the sensor: tungsten probes, glass probes, silicon probe.

The system may also be used to measure other mechanical properties like adhesion forces between to surfaces or friction forces between two surfaces. One sample surface is attached to the sensor and the other one attached to the sample holder. The motion is again generated by the micromanipulators.

A sensor with at least two-axis sensing capabilities may be used to apply a defined force on the sample while moving the sensor sideways. That way shear forces and friction forces can be measured. Cyclic tests may be performed as well.

LIST OF USED REFERENCE NUMERALS, GLOSSARY 1 micromanipulator
2 force sensor; sub-mN resolution capacitive force sensor
3 sample, sample to be tested, sample area; fluid channels
4 adaptor piece
5 sample holder
6 mounting plate
7 microscope positioning table
8 Slide
9 microscope condensor
10 microscope lens
11 microscope camera
12 camera holder
13 stage, manual stage, motorized stage
14 rail
15 sharp probe, sensor probe tip
16 clamps
17 fiber, sample, sample to be tested

LIST OF CITED DOCUMENTS

[1] <<In situ mechanical characterization of mouse oocytes using a cell holding device>>
Xinyu Liu, Roxanne Fernandes, Andrea Jurisicova, Robert F. Casper and Yu Sun
Lab Chip, 2010, 10, 2154-2161.
[2] Mechanical Analysis of Chorion Softening in Prehatching Stages of Zebrafish Embryos
Deok-Ho Kim, Chang Nam Hwang, Yu Sun, Sang Ho Lee, Byungkyu Kim, and Bradley J. Nelson
IEEE TRANSACTIONS ON NANOBIOSCIENCE, VOL. 5, NO. 2, JUNE 2006 89.
[3] A newly designed tensile tester for cells and its application to fibrobroblasts
Hiroshi Miyazaki, Yoshitaka Hasegawa, Kozaburo Hayashi Journal of Biomechanics 33 (2000) 97}104

The invention claimed is:

1. A system for a mechanical characterization of sub-millimeter sized sample areas on a sample holder, the system comprising:
at least one sub-millinewton resolution capacitive force sensor having a sensitive axis;
at least one micromanipulator with position measurement capabilities;
at least one microscope having a given field of view;
at least one sample holder disposed in the field of view of said microscope;
at least one sensor adaptor piece adjustably connecting said force sensor to said micromanipulator at any angular orientation of the sensitive axis relative to said sample holder, said at least one adaptor piece being connected to said micromanipulator by way of screws, slides or a dovetail slide mechanism.

2. The mechanical characterization system according to claim 1, wherein said at least one adaptor piece is one of a plurality of adaptor pieces connected to one another by way of screws, slides or a dovetail slide mechanism.

3. The mechanical characterization system according to claim 1, wherein said microscope is a device selected from the group consisting of a top microscope, a stereo-microscope, an inverted microscope, a microscope camera, a phase-contrast microscope, a confocal microscope, a fluorescence microscope, a scanning electron microscope, and a scanning tunneling microscope.

4. A system for a mechanical characterization of sub-millimeter sized sample areas on a sample holder, the system comprising:
at least one sub-millinewton resolution capacitive force sensor having a sensitive axis;
at least one micromanipulator with position measurement capabilities, said at least one micromanipulator being mounted directly on a fixed base plate;
at least one microscope having a given field of view;
at least one sample holder disposed in the field of view of said microscope;
said force sensor being adjustably connected to said micromanipulator at any angular orientation of the sensitive axis relative to said sample holder.

5. The mechanical characterization system according to claim 4, wherein said sample holder is rigidly connected with said fixed base plate.

6. The mechanical characterization system according to claim 4, wherein said at least one micromanipulator is a multi-axis micromanipulator built up by either linear or rotational micro-manipulators or a combination of both.

7. A system for a mechanical characterization of sub-millimeter sized sample areas on a sample holder, the system comprising:
at least one sub-millinewton resolution capacitive force sensor having a sensitive axis;
a plurality of micro-manipulators with position measurement capabilities each mounted directly on a fixed base plate;
at least one microscope having a given field of view;
at least one sample holder disposed in the field of view of said microscope;
said force sensor being adjustably connected to said micromanipulator at any angular orientation of the sensitive axis relative to said sample holder.

8. The mechanical characterization system according to claim 7, wherein said sample holder is rigidly connected with said fixed base plate.

9. The mechanical characterization system according to claim 7, wherein said micromanipulators are multi-axis micromanipulators built up by either linear or rotational micro-manipulators or a combination of both.

10. A system for a mechanical characterization of sub-millimeter sized sample areas on a sample holder, the system comprising:
- at least one sub-millinewton resolution capacitive force sensor having a sensitive axis;
- at least one micromanipulator with position measurement capabilities;
- at least one microscope having a given field of view;
- at least one sample holder disposed in the field of view of said microscope, said sample holder including a clamp for holding down a sample;
- said force sensor being adjustably connected to said micromanipulator at any angular orientation of the sensitive axis relative to said sample holder.

11. A system for a mechanical characterization of sub-millimeter sized sample areas on a sample holder, the system comprising:
- at least one sub-millinewton resolution capacitive force sensor having a sensitive axis;
- at least one micromanipulator with position measurement capabilities;
- at least one microscope having a given field of view;
- at least one sample holder disposed in the field of view of said microscope;
- said force sensor being adjustably connected to said micromanipulator at any angular orientation of the sensitive axis relative to said sample holder, wherein at least one micromanipulator and said sample holder are mounted on slides for flexible positioning relative to each other.

12. A system for a mechanical characterization of sub-millimeter sized sample areas on a sample holder, the system comprising:
- at least one sub-millinewton resolution capacitive force sensor having a sensitive axis;
- at least one micromanipulator with position measurement capabilities;
- at least one microscope having a given field of view;
- at least one sample holder disposed in the field of view of said microscope, wherein said sample holder includes a fluidic chip for a transportation of samples by fluid flow; and
- said force sensor being adjustably connected to said micromanipulator at any angular orientation of the sensitive axis relative to said sample holder.

13. The mechanical characterization system according to claim 1, wherein said force sensor includes a probe with a defined tip geometry.

14. The mechanical characterization system according to claim 13, wherein said tip of said probe is made of silicon, glass, or tungsten.

* * * * *